United States Patent [19]

Harris et al.

[11] Patent Number: 4,515,978
[45] Date of Patent: May 7, 1985

[54] DIHYDROFURANS

[75] Inventors: Eugene G. Harris, West Chester; Richard G. Fayter, Jr., Fairfield, both of Ohio

[73] Assignee: National Distillers and Chemical Corporation, New York, N.Y.

[21] Appl. No.: 503,974

[22] Filed: Jun. 13, 1983

[51] Int. Cl.³ .................... C07D 307/28; A61K 7/46
[52] U.S. Cl. ................. 549/484; 252/522 R
[58] Field of Search .................... 252/522 R; 549/484

[56] References Cited

U.S. PATENT DOCUMENTS 3,764,567 10/1973 Wakayama et al. ............ 252/522 R

OTHER PUBLICATIONS

Baharel et al., "Chem. Abs.", vol. 75(1971), 87758y.
Wilson et al., "Chem. Abs.", vol. 93(1980), 71095r.
Melikyan et al., "Chem. Abs.", vol. 93(1980), 239,112v.
Vinogradov et al., "Chem. Abs.", vol. 94(1981), 15458v.

Primary Examiner—Anton H. Sutto

Attorney, Agent, or Firm—Kenneth D. Tremain; Gerald A. Baracka

[57] ABSTRACT 2,4,5-Trisubstituted-2,3-dihydrofurans useful as fragrance compounds are provided herein. The compounds of this invention correspond to the general formula

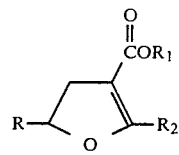

wherein R is an ethyl or vinyl group, $R_1$ is an alkyl group having from 1 to 4 carbon atoms and $R_2$ is a hydrocarbon radical having from 3 to 10 carbon atoms. The 2,3-dihydrofuran compounds of the present invention are useful components in the preparation and formulation of fragranced cosmetic and toiletry products.

6 Claims, No Drawings

DIHYDROFURANS

BACKGROUND OF THE INVENTION

1. Field of the Invention

This invention relates to dihydrofuran derivatives and, more specifically, to certain 2,4,5-substituted-2,3-dihydrofurans which are useful fragrance compounds.

2. Description of the Prior Art

The use of synthetic fragrance chemicals has added a new dimension to the art of perfumery. As a result of the development of new synthetic perfume chemicals, perfumers have greater flexibility in developing fragrance formulations and are better able to mimic natural aromas. However, as perfumers become more adept in the use of synthetic materials for the formulation of sophisticated fragrances and developing the subtle nuances typically associated with natural fragrances, there is a growing demand for new synthetic fragrance compounds.

Furan derivatives are known to have desirable fragrance and flavor qualities. For example, Ethyl furoate, n-amyl furoate, ethyl furyl β-hydroxypropionate and furfural are reported for use in perfumes, cosmetics and soaps. Furfuryl alkyl and aryl ethers are disclosed as flavor enhancers in U.S. Pat. No. 3,940,502. Tetrahydrofurans are also disclosed for fragrance applications. U.S. Pat No. 3,668,134 discloses the use of esters or ethers of tetrahydrofurans as perfumery ingredients for detergent compositions. 3-Oximino-4-oxo-2,5-dimethyl-tetrahydrofuran is described in U.S. Pat. No. 4,116,982 and disclosed to have a fine caramel-like fragrance making it useful for the manufacture of scents and flavors. U.S. Pat. No. 3,470,209 discloses 2-acetonyl-3,5-dimethyl-5-isopropyl-tetrahydrofuran as having a pleasant spicy odor reminiscent of bay and eucalyptus. 2-(1'-Hydroxymethyl-ethyl)-5-methyl-5-vinyl-tetrahydrofuran is disclosed in U.S. Pat. No. 3,764,567 as a useful ingredient for incorporation in floral perfumes. In U.S. Pat. No. 3,227,731 carbonates of 1-(α-furyl)-2,2-dialkyl-1,3-dihydroxypropanes and 1-(α-tetrahydrofuryl)-2,2-dialkyl-1,3-dihydroxypropanes are indicated to be useful in perfume compounding.

2,3-Dihydrofurans having a vinyl group at the 2-position, a lower carboxylate radical at the 4-position and a methyl group at the 5-position have been reported in Chemical Abstracts, Volume 75, 87758y (1971); Volume 93, 71095r (1980); Volume 93, 239112v (1980); and Volume 94, 15458v (1981). Additionally, in Chemical Abstracts Volume 96, 52099r (1982), substituted 2,3-dihydrofurans obtained by the oxidative addition of 1,3-dicarbonyl compounds with dienes in the presence of manganese (III) and copper (II) acetates are reported. None of the reported 2,3-dihydrofurans have a higher alkyl group substituted in the 5-position and there is no indication that any of the compounds have useful fragrance qualities.

SUMMARY OF THE INVENTION

Accordingly, it is an object of this invention to provide novel dihydrofuran derivatives. Another object of the present invention is to provide dihydrofuran derivatives which are useful as fragrance chemicals. Still another object is to provide novel dihydrofuran derivatives which can be readily and economically prepared and which exhibit good stability and diffusivity.

These and other objects are accomplished by providing herein a novel class of 2,4,5-trisubstituted-2,3-dihydrofurans of the general formula

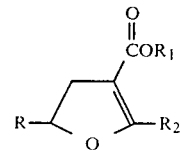

wherein R is an ethyl or vinyl group, $R_1$ is a $C_{1-4}$ alkyl group and $R_2$ is a $C_{3-10}$ hydrocarbon radical which can be aliphatic, cycloaliphatic or aromatic.

DETAILED DESCRIPTION OF THE INVENTION

The 2,4,5-trisubstituted-2,3-dihydrofurans of this invention are useful as fragrance compounds for a variety of applications and have the general formula

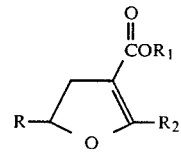

wherein R is an ethyl or vinyl group, $R_1$ is an alkyl group having from 1 to 4 carbon atoms and $R_2$ is a hydrocarbon radical having from 3 to 10 carbon atoms. $R_1$ can be a straight-chain or branched radical such as methyl, ethyl, n-propyl, iso-proyl, n-butyl, tert-butyl and sec-butyl. The hydrocarbon radical $R_2$ can be an aliphatic, cycloaliphatic or aromatic group. When $R_2$ is an aliphatic radical it can be straight-chain or branched and may be saturated or contain unsaturation. Useful cycloaliphatic radicals from which $R_2$ is selected will have from 3 to 6 carbon atoms in the ring and may be saturated or unsaturated. Especially useful cycloaliphatic radicals are the cyclopentyl, cyclohexyl, cyclopentenyl, cyclohexenyl, cyclopentadienyl and cyclohexadienyl which also have one or more alkyl groups substituted thereon. Useful aromatic groups from which $R_2$ is selected include phenyl, benzyl and $C_{1-4}$ alkyl- or $C_{1-4}$ alkoxy-substituted phenyl or benzyl.

Illustrative compounds within the above definition include:
4-carbomethoxy-5-methyl-2-vinyl-2,3-dihydrofuran;
4-carbomethoxy-5-methyl-2-ethyl-2,3-dihydrofuran;
4-carbethoxy-5-methyl-2-ethyl-2,3-dihydrofuran;
4-carbethoxy-5-methyl-2-vinyl-2,3-dihydrofuran;
4-carbomethoxy-5-ethyl-2-vinyl-2,3-dihydrofuran;
4-carbethoxy-5-ethyl-2-ethyl-2,3-dihydrofuran;
4-carbomethoxy-5-n-pentyl-2-vinyl-2,3-dihydrofuran;
4-carbethoxy-5-n-pentyl-2-vinyl-2,3-dihydrofuran;
4-carbethoxy-5-n-pentyl-2-ethyl-2,3-dihydrofuran;
4-carbethoxy-5-(3-methyl-butyl)-2-vinyl-2,3-dihydrofuran;
4-carbethoxy-5-(3-methyl-butyl)-2-ethyl-2,3-dihydrofuran;
4-carbethoxy-5-(4-methyl-3-pentenyl)-2-vinyl-2,3-dihydrofuran;
4-carbethoxy-5-(4-methyl-3-pentenyl)-2-ethyl-2,3-dihydrofuran;
4-carbomethoxy-5-phenyl-2-vinyl-2,3-dihydrofuran;
4-carbethoxy-5-phenyl-2-vinyl-2,3-dihydrofuran;

4-carbethoxy-5-phenyl-2-ethyl-2,3-dihydrofuran;
4-carbomethoxy-5-benzyl-2-vinyl-2,3-dihydrofuran;
4-carbomethoxy-5-benzyl-2-ethyl-2,3-dihydrofuran;
4-carbethoxy-5-(p-tolyl)-2-ethyl-2,3-dihydrofuran;
4-carbethoxy-5-(p-methoxyphenyl)-2-vinyl-2,3-dihydrofuran;
4-carboisopropoxy-5-isopropyl-2-vinyl-2,3-dihydrofuran;
4-carboisopropoxy-5-isopentenyl-2-ethyl-2,3-dihydrofuran; and the like.

Particularly useful 2,4,5-trisubstituted-2,3-dihydrofurans, in view of their highly desirable fragrance characteristics, are those compounds where R is ethyl or vinyl, $R_1$ is methyl or ethyl and $R_2$ is a $C_{3-8}$ alkyl or alkenyl group.

The 2,3-dihydrofurans of this invention are generally characterized as having a pleasing, natural fragrance. By varying the ring substituents, it is possible to mimic a number of natural aromas such as, for example, woody, herbaceous, green, nutty, fruity or vegetable aromas. Most typically several of these notes will be present in the fragrance even though one note may be predominant. These fragrances are intense, without being overwhelming, and have good diffusivity, stability and dryout characteristics.

The 2,4,5-trisubstituted-2,3-dihydrofurans are useful components in the preparation and formulation of fragranced products such as perfumes, shampoos, deodorants, having creams and gels, body lotions and creams, detergent and bar soaps, and the like. They may be employed as the sole fragrance material but most generally are used in conjunction with other fragrance materials. When combined with other fragrance materials, the 2,3-dihydrofuran will be present from trace amounts up to about 50 percent of the fragrance formulation, depending on the particular fragrance desired and the end-use application.

The novel 2,3-dihydrofuran derivatives of the present invention are obtained by isomerization of the corresponding cyclopropyl ketone derivative in accordance with the following general equation.

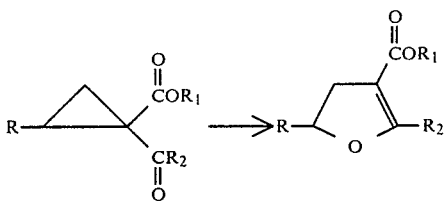

wherein R, $R_1$, and $R_2$ are the same as previously defined. The isomerization process is fully described in the co-pending application Ser. No. 503,974, filed June 13, 1983, of R. G. Fayter, Jr. and A. L. Hall entitled PROCESS FOR THE ISOMERIZATION OF CYCLOPROPYL KETONES TO 2,3-DIHYDROFURANS and filed on the same date as the present application-details of which are incorporated herein by reference thereto.

The isomerization is typically carried out at a temperature from 60° C. to 200° C. utilizing from about 0.5 to 20 weight percent, based on the cyclopropyl ketone, of an onium catalyst. Most generally, the onium catalyst is present in an amount from 2 to 15 weight percent and is a quaternary ammonium or phosphonium compound containing at least six carbon atoms and corresponding to the formula

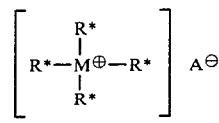

where M is nitrogen or phosphorous, R* represents a hydrocarbon radical having from 1 to 22 carbon atoms, and A is chloride or bromide. Particularly useful onium catalysts for the isomerization process contain at least 10 carbon atoms and include tetrabutylammonium chloride; tetrabutylammonium bromide; dimethyldibenzylammonium chloride; dimethyldibenzylammonium bromide; trimethylbenzylammonium chloride; trimethylbenzylammonium bromide; tricaprylylmethylammonium chloride; tricaprylylmethylammonium bromide; tributylhexadecylphosphonium chloride; tributylhexadecylphosphonium bromide; and the like.

Preferably, the isomerization reaction is carried out in the absence of a diluent or solvent and the cyclopropyl ketone should be essentially free of water, caustic or salts. If a solvent or diluent is employed, it must be inert to the reaction conditions and must be separated from the 2,3-dihydrofuran at the conclusion of the reaction by distillation or the like. It is also preferred to remove the onium catalyst from the 2,3-dihydrofuran, particularly where critical fragrance applications are involved.

The following examples illustrate the invention more fully. In the examples, all parts and percentages are on a weight basis unless otherwise indicated.

EXAMPLE I

In accordance with the phase transfer procedure of U.S. Pat. No. 4,252,739, ethyl 2-vinyl-1-hexanoylcyclopropane-1-carboxylate was obtained from the reaction of 0.53 mole ethyl hexanoyl acetate

0.66 mole 1,4-dichlorobutene-2, and 1.06 moles potassium hydroxide. The reaction was carried out in a mixture of water and methylene chloride utilizing 0.0133 mole tricaprylylmethylammonium chloride as the phase transfer catalyst. The resulting reaction product was then filtered through a sintered glass funnel to remove excess potassium hydroxide and insoluble salts formed during the reaction and neutralized with 10 percent sulfuric acid. The crude product obtained after drying and removal of the methylene chloride contained approximately 95 percent ethyl 2-vinyl-1-hexanoylcyclopropane-1-carboxylate.

The ethyl 2-vinyl-1-hexanoylcyclopropane-1-carboxylate obtained above (120 grams) was combined with 25.6 grams tricaprylylmethylammonium chloride and heated at 110° C. under a nitrogen atmosphere with agitation to isomerize the cyclopropyl ketone to the corresponding 2,3-dihydrofuran. After three hours, gas chromatographic analysis showed the reaction mixture to contain 41 percent 4-carbethoxy-5-n-pentyl-2-vinyl-2,3-dihydrofuran. Heating was continued at 110° C. until the 4-carbethoxy-5-n-pentyl-2-vinyl-2,3-dihydrofuran content was increased to 87 percent. By distillation it was possible to obtain essentially pure 4-carbethoxy-5-n-pentyl-2-vinyl-2,3-dihydrofuran. The 4-carbethoxy-5-n-pentyl-2-vinyl-2,3-dihydrofuran was a clear, colorless liquid (B.P. 103°–109° C. @ 2 mm Hg, $n_D^{25°}$ 1.4709) and had a pleasing fragrance useful in Jasmone and/or citrus formulations.

nmr(CDCl$_3$) δ 1.28 (t, 3H($\underline{CH}_3$—CH$_2$—O—CO)); 4.23 (q, 2H(CH$_3$—$\underline{CH}_2$—O—CO—)); 0.90 (t, 3H($\underline{CH}_3$—CH$_2$—CH$_2$—)); 1.10–1.80 (m, 6 methylene H); 2.50–3.55 (m, 2 ring methylene H), 2.70 (br.t., (2 methylene H adj. to ring)); 4.80–5.55 (m, 3 vinyl H), 5.70–6.34 (m, 1 ring H).

IR (film) 2960, 2930, 2870, 1695, 1637, 1370, 1252, 1225, 1173, 1104, 1050, 970 and 767 cm$^{-1}$.

EXAMPLE II

4-Carbethoxy-5-n-pentyl-2-vinyl-2,3-dihydrofuran prepared in accordance with the procedure of Example I was hydrogenated to obtain 4-carbethoxy-5-n-pentyl-2-ethyl-2,3-dihydrofuran. For the reaction, 13 grams 4-carbethoxy-5-n-pentyl-2-vinyl-2,3-dihydrofuran and 75 mls ethyl acetate were charged to the reactor of a Parr apparatus. The system was thoroughly purged with nitrogen and 0.65 gram of a hydrogenation catalyst (5 percent palladium on carbon) added under a nitrogen atmosphere. After additional nitrogen purging, shaking was begun and the system pressurized with hydrogen to 15 psig. The system was repressurized as necessary until no further hydrogen uptake was noted. The reaction mixture was then filtered through Dicalite ® to remove the Pd/carbon catalyst and ethyl acetate removed under reduced pressure. Gas chromatographic analysis indicated 98 percent yield crude 4-carbethoxy-5-n-pentyl-2-ethyl-2,3-dihydrofuran. The crude product was fractionated using a spinning-band distillation apparatus to obtain essentially pure 4-carbethoxy-5-n-pentyl-2-ethyl-2,3-dihydrofuran (B.P. 112°–114° C. @ 1 mm Hg; $n_D^{25°}$ 1.4636); which was confirmed by nuclear magnetic resonance and infrared spectroscopic analysis.

nmr (CDCl$_3$) δ 1.29 (t, 3H ($\underline{CH}_3$—CH$_2$—O—CO—)); 4.19 (q, 2H (CH$_3$—$\underline{CH}_2$—O—CO—)); 0.60–1.95 (m, 14H (—CH$_2$—$\underline{CH}_2$ and $\underline{CH}_3$—CH$_2$-type hydrogens)); 2.30–3.42 (m, 2 ring methylene H); 2.68 (br.t., (2 methylene H adj. to ring)); 4.30–4.95 (m, 1 ring H).

IR (film) 2970, 2930, 2870, 1694, 1636, 1462, 1370, 1330, 1255, 1228, 1173, 1104, 1048, 973 and 765 cm$^{-1}$.

The 4-carbethoxy-5-n-pentyl-2-ethyl-2,3-dihydrofuran had notes compatible with and suitable for blending in Jasmone and citrus compositions.

EXAMPLE III

In a manner similar to that described in Example I, 4-carbethoxy-5-(3-methyl-butyl)-2-vinyl-2,3-dihydrofuran was prepared by the isomerization of ethyl 2-vinyl-1-(4-methylpentanoyl)cyclopropane-1-carboxylate. For the reaction, 125 mls of the ethyl 2-vinyl-1-(4-methylpentanoyl)cyclopropane-1-carboxylate was combined with 25.4 grams tricaprylylmethylammonium chloride. The mixture was stirred at 100° C. for approximately eleven hours, after which time gas chromatographic analysis showed the reaction mixture to obtain about 85 percent 4-carbethoxy-5-(3-methyl-butyl)-2-vinyl-2,3-dihydrofuran. Heating was terminated and the crude product distilled using a spinning-band distillation apparatus fitted with a 12 inch column. Essentially pure 4-carbethoxy-5-(3-methyl-butyl)-2-vinyl-2,3-dihydrofuran was obtained (B.P. 101°–102° C. @ 1 mm Hg; $n_D^{25°}$ 1.4742). The 4-carbethoxy-5-(3-methyl-butyl)-2-vinyl-2,3-dihydrofuran had a pleasing fragrance with a slightly weedy, fatty, nutty-scotch whiskey odor profile.

nmr (CDCl$_3$) δ 1.27 (t, 3H ($\underline{CH}_3$—CH$_2$—O—CO—)); 4.23 (q, 2H (CH$_3$—$\underline{CH}_2$—O—CO—)); 0.90 (d, 6H (($\underline{CH}_3$)$_2$—CH)); 1.22–1.82 (m, 3H (—CH$_2$—CH$_2$—$\underline{CH}$—)); 2.68 (br. t, 2H (2 methylene H adj. to ring)); 2.40–3.40 (m, 2 ring methylene H); 4.85–5.60 (m, 3 vinyl H); 5.78–6.40 (m, 1 ring H).

IR (film) 2959, 2930, 2875, 1699, 1636, 1369, 1311, 1250, 1234, 1192, 1172, 1135, 1107, 1054, 970 and 765 cm$^{-1}$

EXAMPLE IV

4-Carbethoxy-5-(3-methyl-butyl)-2-vinyl-2,3-dihydrofuran prepared in accordance with Example III was hydrogenated to obtain 4-carbethoxy-5-(3-methyl-butyl)-2-ethyl-2,3-dihydrofuran. The hydrogenation procedure employed was the same as described in Example II. After removal of the catalyst and ethyl acetate, 17.47 grams crude 4-carbethoxy-5-(3-methyl-butyl)-2-ethyl-2,3-dihydrofuran was obtained. Distillation of the crude hydrogenated material yielded essentially pure 4-carbethoxy-5-(3-methyl-butyl)-2-ethyl-2,3-dihydrofuran boiling at 102° C.–103° C. at 0.6 mm Hg ($n_D^{25°}$ 1.4621). The material had an intense fruity odor-strawberry and apple predominating, with traces of chamomile.

nmr (CDCl$_3$) δ 1.28 (t, 3H ($\underline{CH}_3$—CH$_2$—O—CO—)); 4.21 (q, 2H (CH$_3$—$\underline{CH}_2$—O—CO—)); 0.93 (d, 6H ($\underline{CH}_3$)$_2$—CH—)); 0.71–1.86 (m (complex), 8H; 2.68 (br.t, 2H (2 methylene H adj. to ring)); 2.26–3.31 (m, 2 ring methylene H); 4.28–5.01 (m, 1 ring H).

IR (film) 2980, 2955, 2900, 1705, 1640, 1472, 1375, 1340, 1265, 1240, 1175, 1145, 1110, 1055, 970 and 770 cm$^{-1}$.

EXAMPLE V

In a manner similar to that previously described, ethyl 2-vinyl-1-(5-methyl-4-hexenoyl)cyclopropane-1-carboxylate, obtained by the condensation of ethyl 5-methyl-4-hexenoylacetate and 1,4-dichlorobutene-2 under phase transfer conditions, was isomerized to obtain 4-carbethoxy-5-(4-methyl-3-pentenyl)-2-vinyl-2,3-dihydrofuran. The isomerization was carried out at 110° C. under a nitrogen atmosphere using 19.6 weight percent tricaprylylmethylammonium chloride catalyst. After about three hours, chromatographic analysis confirmed the presence of 92 percent 4-carbethoxy-5-(4-methyl-3-pentenyl)-2-vinyl-2,3-dihydrofuran in the reaction mixture. Distillation of the isomerized product afforded 15 grams pure 4-carbethoxy-5-(4-methyl-3-pentenyl)-2-vinyl-2,3-dihydrofuran (B.P. 104°–110° C. @ 0.6 mm Hg; $n_D^{25°}$ 1.4910). The clear, colorless liquid had a somewhat hedge-like aroma with a chamomile-like nuance.

nmr (CDCl$_3$) δ 1.30 (t, 3H ($\underline{CH}_3$—CH$_2$—O—CO—)); 4.25 (q, 2H (CH$_3$—$\underline{CH}_2$—O—CO—)), 1.68 (d, 6H ($\underline{CH}_3$)$_2$=CH—)); 2.42 (br.t, 2H (—$\underline{CH}_2$—CH=C(CH$_3$)$_2$)); 2.75 (br.t, 2H (2 methylene H adj. to ring)); 2.40–3.45 (m, 2 ring methylene H, part. hidden); 4.85–5.60 (m, 4 vinyl H); 5.77–6.37 (m, 1 ring H).

IR (film) 2975, 2920, 2875, 1691, 1633, 1447, 1372, 1310, 1232, 1155, 1107, 1065, 1025, 972, 915 and 765 cm$^{-1}$.

EXAMPLE VI

4-Carbethoxy-5-(4-methyl-3-pentenyl)-2-vinyl-2,3-dihydrofuran of Example V was hydrogenated to obtain 4-carbethoxy-5-(4-methyl-3-pentenyl)-2-ethyl-2,3-dihydrofuran. Five percent by weight catalyst (5% Pd on a carbon support) was used. The hydrogenation was essentially complete in three hours. After removal of the catalyst and ethyl acetate solvent, the crude hydrogenated product was distilled using a 50-plate spinning-band distillation apparatus to provide essentially pure 4-carbethoxy-5-(4-methyl-3-pentenyl)-2-ethyl-2,3-dihydrofuran (B.P. 58° C. @ 0.01 mm Hg; $n_D^{25°}$ 1.4791). The product had a nutty character and was smoother in overall odor quality than the unsaturated parent disclosed in Example V.

nmr (CDCl$_3$) δ 1.28 (t, 3H (C$\underline{H}_3$—CH—O—CO—)); 4.22 (q, 2H (CH$_3$—C$\underline{H}_2$—O—CO—)); 0.98 (t, 3H (C$\underline{H}_3$—CH$_2$—C—)); 1.33–1.70 (q, 2H (CH$_3$—C$\underline{H}_2$—C—) hidden); 1.68 (d, 6H ((C$\underline{H}_3$)$_2$C=CH—)); 2.35 (br.t, 2H (—C$\underline{H}_2$—CH=C(CH$_3$)$_2$)); 2.73 (br.t, 2H (2 methylene H $\overline{\text{adj.}}$ to ring)); 2.30–3.35 (m, 2 ring methylene H, part. hidden); 4.30–4.80 (m, 1 ring H); 5.23 (br.t, 1 vinyl H).

IR (film) 2970, 2930, 2875, 1690, 1635, 1450, 1373, 1236, 1156, 1107, 1066, 1026, 985, 830 and 765 cm$^{-1}$.

EXAMPLE VII

4-Carbethoxy-5-phenyl-2-vinyl-2,3-dihydrofuran was obtained in the usual manner by isomerizing ethyl 2-vinyl-1-benzoylcyclopropane-1-carboxylate. To catalyze the isomerization, tricaprylylmethylammonium chloride was employed at a 20 percent weight level. The mixture was heated at 150° C. for about two hours after which time only about 7 percent of the cyclopropyl ketone remained. After two distillations of the resulting isomerized product, essentially pure 4-carbethoxy-5-phenyl-2-vinyl-2,3-dihydrofuran was obtained (B.P. 110° C. @ 0.1 mm Hg; $n_D^{25°}$ 1.5570). The product had a pleasing aroma that was somewhat coumarin-like in odor character.

nmr (CDCl$_3$) δ 1.20 (t, 3H (C$\underline{H}_3$—CH$_2$—O—CO—)); 4.17 (q, 2H (CH$_3$—C$\underline{H}_2$—O—$\overline{\text{CO}}$—)); 2.70–3.60 (oct, 2 ring methylene H); $\overline{2.93}$–5.60 (m, 3 vinyl H); 5.80–6.45 (m, 1 ring H); 7.30–8.15 (m, 5 phenyl H).

IR (film) 2980, 1697, 1622, 1598, 1496, 1446, 1370, 1240, 1085, 1070, 987, 926, 760 and 695 cm$^{-1}$.

We claim:

1. A compound of the formula

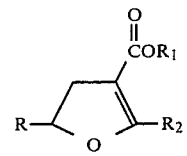

wherein R is vinyl, R$_1$ is a C$_{1-4}$ alkyl group and R$_2$ is a C$_{3-8}$ alkyl or alkenyl group.

2. The compound of claim 1 wherein R$_1$ is methy or ethyl.

3. The compound of claim 1 which is 4-carbethoxy-5-n-pentyl-2-vinyl-2,3-dihydrofuran.

4. The compound of claim 1 which is 4-carbethoxy-5-(3-methylbutyl)-2-vinyl-2,3-dihydrofuran.

5. The compound of claim 1 which is 4-carbethoxy-5-(4-methyl-3-pentenyl)-2-vinyl-2,3-dihydrofuran.

6. 4-Carbethoxy-5-phenyl-2-vinyl-2,3-dihydrofuran.

* * * * *

UNITED STATES PATENT AND TRADEMARK OFFICE
CERTIFICATE OF CORRECTION

PATENT NO. : 4,515,978

DATED : May 7, 1985

INVENTOR(S) : E. G. Harris and R. G. Fayter, Jr.

It is certified that error appears in the above-identified patent and that said Letters Patent are hereby corrected as shown below:

Column 2, line 34, "iso-proyl" should read --- iso-propyl ---.

Column 3, line 30, "having" should read --- shaving ---; line 56, "503,974" should read --- 503,952 ---.

Column 6, line 12, --- . --- should be inserted after "$cm^{-1}$"; line 32, "(m (complex)" should read --- (m, complex) ---; line 61, ",", second instance, should be --- ; ---.

Column 8, line 26, "methy" should read --- methyl ---.

Signed and Sealed this

First Day of October 1985

[SEAL]

Attest:

Attesting Officer

DONALD J. QUIGG

*Commissioner of Patents and Trademarks—Designate*